(12) United States Patent
Li et al.

(10) Patent No.: US 10,013,969 B2
(45) Date of Patent: Jul. 3, 2018

(54) ACOUSTIC LENS FOR MICROMACHINED ULTRASOUND TRANSDUCERS

(71) Applicant: FUIJIFILM SonoSite, Inc., Bothell, WA (US)

(72) Inventors: Wei Li, Bothell, WA (US); Paul Dunham, Bothell, WA (US); Chak-Yoon Aw, Shoreline, WA (US); N. Chris Chaggares, Whitby (CA)

(73) Assignee: FUJIFILM Sonosite, Inc., Bothell, WA (US)

( * ) Notice: Subject to any disclaimer, the term of this patent is extended or adjusted under 35 U.S.C. 154(b) by 51 days.

(21) Appl. No.: 15/353,720

(22) Filed: Nov. 16, 2016

(65) Prior Publication Data

US 2017/0133004 A1 May 11, 2017

Related U.S. Application Data

(63) Continuation of application No. 14/205,123, filed on Mar. 11, 2014, now Pat. No. 9,502,023.
(Continued)

(51) Int. Cl.
*B06B 1/06* (2006.01)
*G01N 29/14* (2006.01)
(Continued)

(52) U.S. Cl.
CPC ............ *G10K 11/30* (2013.01); *B06B 1/0292* (2013.01); *B06B 1/0611* (2013.01);
(Continued)

(58) Field of Classification Search
CPC ...... G10K 11/30; G10K 11/168; G10K 9/122; B06B 1/0292; B06B 1/0611;
(Continued)

(56) References Cited

U.S. PATENT DOCUMENTS

| 3,482,122 A | 12/1969 | Lenahan |
| 4,523,122 A | 6/1985 | Tone et al. |

(Continued)

FOREIGN PATENT DOCUMENTS

| CN | 101605288 A | 12/2009 |
| CN | 101896288 A | 11/2010 |

(Continued)

OTHER PUBLICATIONS

Japanese Patent Office, Official Action, JP Patent Application 2014-051733, dated Sep. 13, 2017, 18 pages; includes English translation.
(Continued)

*Primary Examiner* — Thomas Dougherty
(74) *Attorney, Agent, or Firm* — Perkins Coie LLP

(57) ABSTRACT

Matching layers configured for use with ultrasound transducers are disclosed herein. In one embodiment, a transducer stack can include a capacitive micromachined ultrasound transducer (CMUT), an acoustic lens, and a matching layer therebetween. The matching layer can be made from a compliant material (e.g. an elastomer and/or an liquid) and configured for use with CMUTs. The matching layer can include a bottom surface overlying a top surface of the transducer and a top surface underlying a bottom surface of the lens.

16 Claims, 4 Drawing Sheets

Related U.S. Application Data

(60) Provisional application No. 61/793,124, filed on Mar. 15, 2013.

(51) Int. Cl.
*G01N 29/28* (2006.01)
*G10K 11/30* (2006.01)
*G10K 11/168* (2006.01)
*H01L 41/08* (2006.01)
*B81B 3/00* (2006.01)
*B06B 1/02* (2006.01)
*G01N 29/24* (2006.01)

(52) U.S. Cl.
CPC ....... *B81B 3/0021* (2013.01); *G01N 29/2406* (2013.01); *G01N 29/2437* (2013.01); *G10K 11/168* (2013.01); *H01L 41/0825* (2013.01); *B81B 2201/02* (2013.01)

(58) Field of Classification Search
CPC .............. B81B 3/0021; G01N 29/2406; G01N 29/2437; H01L 41/0825; H04R 17/00; H03H 9/09; F16F 5/0058
USPC ......................... 310/322, 326, 327, 334, 335
See application file for complete search history.

(56) References Cited

U.S. PATENT DOCUMENTS

| | | | |
|---|---|---|---|
| 5,353,798 A | 10/1994 | Sieben | |
| 5,365,024 A | 11/1994 | Hasegawa et al. | |
| 5,553,035 A | 9/1996 | Seyed-Bolorforosh et al. | |
| 6,183,578 B1 | 2/2001 | Ritter et al. | |
| 6,551,247 B2 | 4/2003 | Saito et al. | |
| 6,822,376 B2 | 11/2004 | Baumgartner | |
| 6,851,392 B2 | 2/2005 | Zan et al. | |
| 7,133,713 B2 | 11/2006 | Zan | |
| 7,139,676 B2 | 11/2006 | Barford | |
| 7,230,368 B2 | 6/2007 | Lukacs et al. | |
| 7,426,904 B2 | 9/2008 | Zan et al. | |
| 7,794,401 B2 | 9/2010 | Tanaka et al. | |
| 8,343,289 B2 | 1/2013 | Chaggares et al. | |
| 9,502,023 B2 * | 11/2016 | Li | B06B 1/0292 |
| 2002/0111620 A1 | 8/2002 | Cooper et al. | |
| 2002/0180316 A1 | 12/2002 | Linden et al. | |
| 2003/0032884 A1 | 2/2003 | Smith et al. | |
| 2004/0000847 A1 | 1/2004 | Ladabaum et al. | |
| 2004/0095045 A1 | 5/2004 | Baumgartner | |
| 2004/0236219 A1 | 11/2004 | Liu et al. | |
| 2005/0075571 A1 | 4/2005 | Barnes et al. | |
| 2005/0075572 A1 | 4/2005 | Mills et al. | |
| 2005/0127793 A1 | 6/2005 | Baumgartner et al. | |
| 2005/0272183 A1 | 12/2005 | Lukacs et al. | |
| 2006/0004290 A1 | 1/2006 | Smith et al. | |
| 2007/0205698 A1 | 9/2007 | Chaggares et al. | |
| 2007/0222338 A1 | 9/2007 | Aono et al. | |
| 2008/0064959 A1 | 3/2008 | Kanda et al. | |
| 2008/0275344 A1 | 11/2008 | Glide-Hurst et al. | |
| 2009/0076392 A1 | 3/2009 | Oshiki et al. | |
| 2010/0168583 A1 | 7/2010 | Dausch et al. | |
| 2010/0234736 A1 | 9/2010 | Corl et al. | |
| 2010/0256498 A1 | 10/2010 | Tanaka et al. | |
| 2010/0268081 A1 | 10/2010 | Asafusa et al. | |
| 2012/0123268 A1 | 5/2012 | Tanaka et al. | |
| 2012/0262770 A1 | 10/2012 | Torashima et al. | |

FOREIGN PATENT DOCUMENTS

| | | |
|---|---|---|
| CN | 102596431 A | 7/2012 |
| JP | 56086598 | 7/1981 |
| JP | 58-058013 | 4/1983 |
| JP | 58171665 | 10/1983 |
| JP | 02260999 | 10/1990 |
| JP | 09107594 | 4/1997 |
| JP | H10170686 A | 6/1998 |
| JP | 2001069594 | 3/2001 |
| JP | 2001069594 A | 3/2001 |
| JP | 2005198261 | 7/2005 |
| JP | 2006174992 A | 7/2006 |
| JP | 2007259165 A | 10/2007 |
| JP | 2007534277 A | 11/2007 |
| JP | 2009112379 A | 5/2009 |
| JP | 2009528783 A | 8/2009 |
| JP | 2012520127 A | 9/2012 |
| JP | 2012222785 A | 11/2012 |
| WO | 2005104210 | 11/2005 |

OTHER PUBLICATIONS

State Intellectual Property Office of China, Third Office Action, CN Patent Application 201410097886.6, dated Aug. 23, 2017, 12 pages (includes English translation).
State Intellectual Property Office of China, First Office Action, CN Patent Application 201410097886.6, dated Feb. 25, 2016, 15 pages (including English translation).
Callens, D. et al. "Matching ultrasonic transducer using two matching layers where one of them is glue." NDT & E International, Butterworth-Heinemann, Oxford, GB. Dec. 1, 2004, vol. 37, No. 8, pp. 591-596.
Extended Search Report for European Patent Application No. EP 07752028,6, dated Mar. 29, 2012, 7 pages.
First Office Action for Chinese Patent Application CN 200780016016.X, dated Jun. 8, 2010, 8 pages.
International Search Report and Written Opinion, PCT Application US2007/005300, dated Feb. 14, 2008, 7 pages.
Notice of Reasons for Rejection for Japanese Patent Application JP 2008-557385, dated Oct. 6, 2011, 6 pages.
Second Office Action for Chinese Patent Application CN 200780016016.X, dated Jan. 12, 2011, 16 pages.
State Intellectual Property Office of China, Second Office Action, CN Patent Application 201410097886.6, dated Dec. 27, 2016, 19 pages (including English translation).

* cited by examiner

ACOUSTIC LENS FOR MICROMACHINED ULTRASOUND TRANSDUCERS

CROSS-REFERENCES TO RELATED APPLICATIONS

This application is a continuation of U.S. patent application Ser. No. 14/205,123, filed on Mar. 11, 2014, now U.S. Pat. No. 9,502,023, entitled "ACOUSTIC LENS FOR MICROMACHINED ULTRASOUND TRANSDUCERS," which claims benefit of U.S. Provisional Patent Application Ser. No. 61/793,124, filed on Mar. 15, 2013, and entitled "ACOUSTIC LENS FOR MICROMACHINED ULTRASOUND TRANSDUCERS," both of which are hereby incorporated herein in their entireties by reference.

TECHNICAL FIELD

The disclosed technology relates generally to ultrasound transducers, and more specifically matching layers for ultrasound transducers.

BACKGROUND

In ultrasound imaging devices, images of a subject are created by transmitting one or more acoustic pulses into the body from a transducer. Reflected echo signals that are created in response to the pulses are detected by the same or a different transducer. The echo signals cause the transducer elements to produce electronic signals that are analyzed by the ultrasound system in order to create a map of some characteristic of the echo signals such as their amplitude, power, phase or frequency shift etc. The map therefore can be displayed to a user as images.

One class of transducer is a Micromachined Ultrasound Transducer (MUT), which can be fabricated from, for example, silicon and configured to transmit and receive ultrasound energy. MUTs may include Capacitive Micromachined Ultrasound Transducer (CMUTs) and Piezoelectric Micromachined Ultrasound Transducer (PMUTs). MUTs can offer many advantages over other conventional transducers such as, for example, lower cost of production, decreased fabrication time, and/or wider frequency bandwidth. MUTs, however, can be fragile and are typically utilized in single-use internal ultrasound imaging applications.

The use of a transducer in an external probe generally involves bonding or otherwise attaching an acoustic lens to the transducer. The acoustic lens can protect the transducer from damage and/or may also provide acoustic focusing into a subject. In some low frequency applications, MUTs may be utilized in external probes having acoustic lenses made from, for example, an elastomer material. However, these elastomer lenses may not be suitable for high frequency ultrasound applications (e.g., greater than about 15 MHz) due to, among other reasons, increased acoustic attenuation of the materials at the higher frequencies. Accordingly, a need for a low-loss and durable acoustic lens exists for an external MUT probe suitable for use at higher frequencies.

DETAILED DESCRIPTION

The present technology is generally directed to matching layers configured for use with ultrasound transducers. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with reference to FIGS. 1-4B.

Capturing ultrasound data from a subject using an exemplary transducer stack generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

The disclosed transducers can be operatively connected to an ultrasound imaging system for the generation, transmission, receipt, and processing of ultrasound data. For example, ultrasound can be transmitted, received and processed using an ultrasonic scanning device that can supply an ultrasonic signal of any frequency. In some aspects of the present disclosure, an ultrasound system or device capable of operating at 15 MHz or above can be used, while in other aspects ultrasound systems or devices configured to operate below 15 MHz may also be used. While the transducers disclosed below may be used in ultrasonic medical measurement and/or imaging applications, they are not limited to such uses. In some embodiments, for example, the transducers below can be used in biometric applications, such as, for example, fingerprint scanners.

Figure 1:
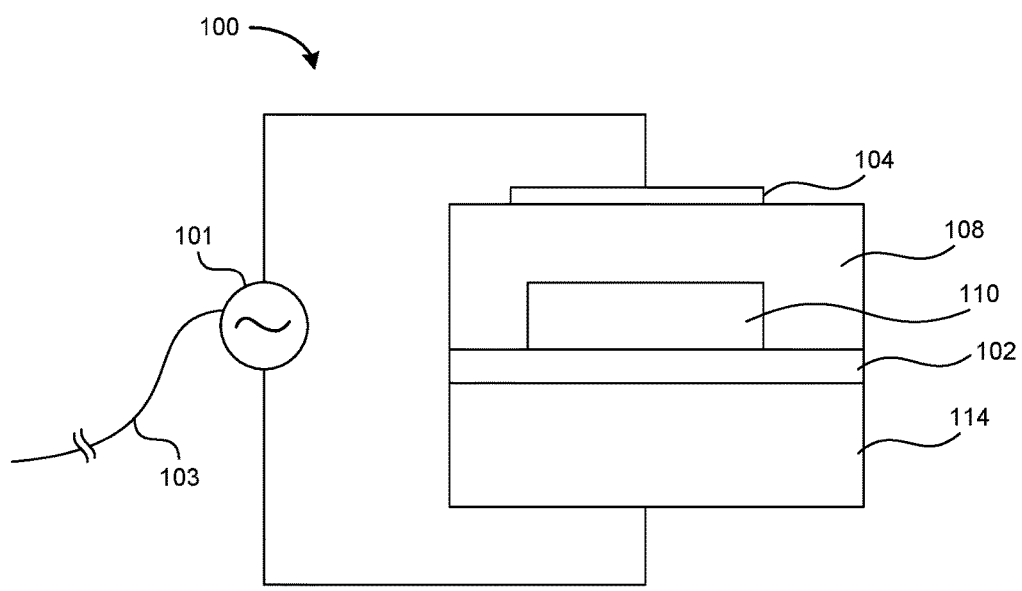
FIG. 1 is a side schematic view of a prior art Capacitive Micromachined Ultrasound Transducer.

FIG. 1 is a side view of an ultrasound transducer 100 configured in accordance with an embodiment of the disclosed technology. The transducer 100 includes an electric power source 101 coupled to a top electrode 104 and a bottom electrode 102 deposited on a substrate 114 (e.g., a silicon substrate). The top electrode 104 is coupled to or otherwise adjacent to a membrane 108. As explained in further detail below, the top electrode 104 can be configured to cause deflections in the membrane 108, which can, for example, cause an ultrasound wave to propagate therefrom. A gap 110 allows the membrane 108 to deflect sufficiently downward (e.g., toward the bottom electrode 102) without coming into contact with the bottom electrode 102 and/or the substrate 114. The membrane 108 may deflect in response to, for example, a change in voltage between the bottom and top electrodes 102 and 104 and/or acoustic energy (e.g. ultrasound waves) incident on the membrane 108.

In the illustrated embodiment, the transducer 100 is configured as a Capacitive Micromachined Ultrasound Transducer (CMUT). As those of ordinary skill in the art will appreciate, a bias voltage may be applied by the power source 101 to the top electrode 104 and the bottom electrode 102. The power source 101 can include an alternating current source and/or a direct current source (not shown). Acoustic energy (e.g., ultrasound waves) striking the transducer 100 can deflect the membrane 108, causing variations in the voltage between the top and bottom electrodes 102 and 104 to generate an electric signal. Conversely, applying an alternating current signal between the top and bottom electrodes 102 and 104 can deflect the membrane 108 to generate an ultrasound signal that can propagate away from the transducer 100.

Figure 2A:
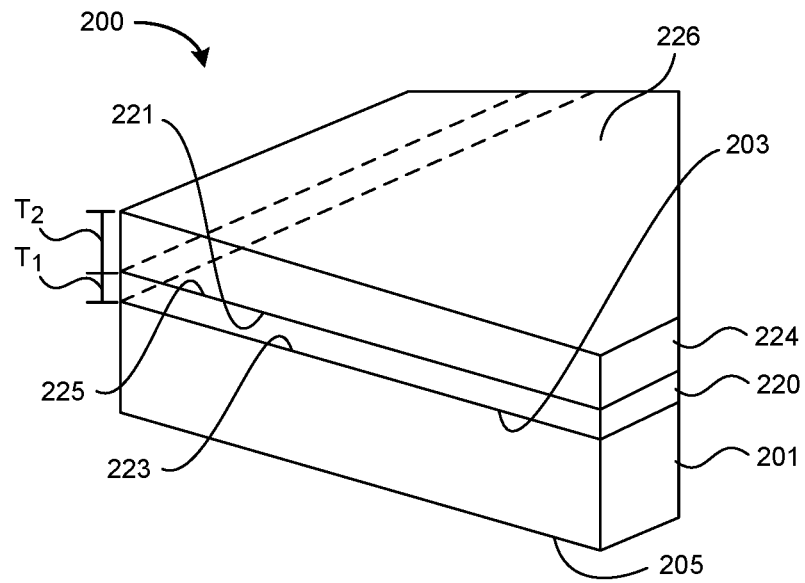
FIG. 2A is an isometric front view of an ultrasound transducer stack configured in accordance with one or more embodiments of the disclosed technology.

FIG. 2A is a isometric front view of an ultrasound transducer stack 200 configured in accordance with embodiments of the disclosed technology. The transducer stack 200 includes a transducer layer 201 below a first layer 220 and a second layer 224. The transducer 201 may comprise, for example, a single array element, one-dimensional array of transducer elements, or a multi-dimensional array of transducer elements. Moreover, the transducer 201 may be made from any suitable transducer known in the art, such as, for example, piezoelectric transducers, CMUTs, piezoelectric micromachined ultrasound transducers (PMUTs), etc. A transducer top surface 203 underlies a first layer bottom surface 223, and a first layer top surface 221 underlies a second layer bottom surface 225. A second layer top surface 226 can be applied to or placed proximate to a subject (e.g., a human, an animal, etc.).

Figure 2B:
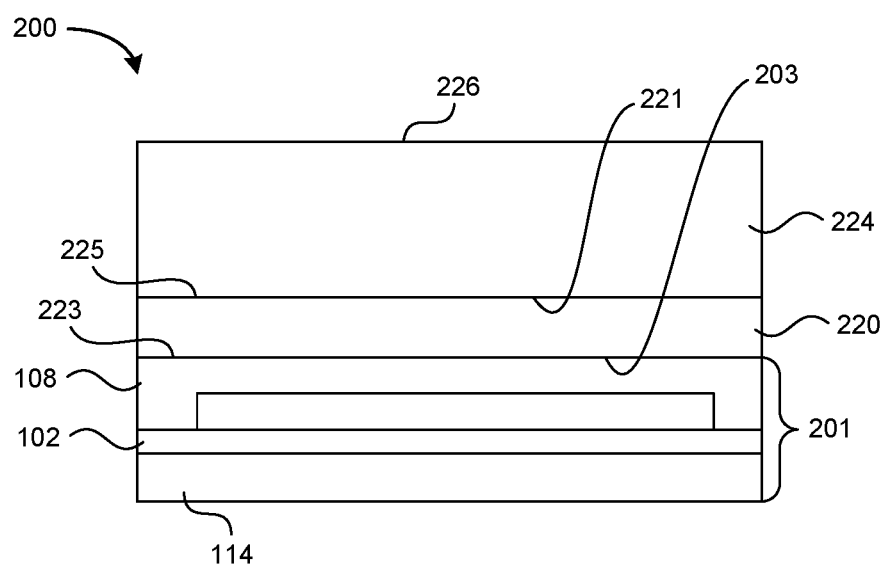
FIG. 2B is an enlarged side view of an ultrasound transducer stack configured in accordance with an embodiment of the disclosed technology.

FIG. 2B is a side view of the transducer stack 200 configured in accordance with an embodiment of the disclosure. In the illustrated embodiment, the transducer layer includes a CMUT (e.g., the transducer 100 of FIG. 1). As those of ordinary skill in the art will appreciate, CMUT transducers (e.g., the transducer 201) can be fragile and may lack the durability of other types of transducers (e.g., PZT transducers). However, placing a low acoustic loss and durable stiff material directly onto a CMUT transducer can significantly reduce the efficiency of the array and may prevent the array from even functioning. Accordingly, as described in further detail below, assembling an ultrasound transducer stack with a relatively thin compliant layer (e.g., the first layer 220) between the lens (e.g. the second layer 224) and the transducer (e.g., transducer 201) allows the transducer to emit ultrasound efficiently while also bonding the transducer 201 to the second layer 224. Furthermore, bonding a stiff outer layer can also maintain the flatness of the transducer, thereby improving transducer efficiency and accuracy.

Referring to FIGS. 2A and 2B together, the first layer 220 is made from a compliant material (e.g., a PDMS-type silicone) configured to join or otherwise couple the second layer 224 to the transducer 201. In other embodiments, however, the first layer 220 can be made from, for example, any material suitable for matching layers known in the art, such as, for example, an elastomer, a gel, a polymerized material, etc. In further embodiments, the first layer 220 may be made from any suitable fluid such as, for example, water, an oil, etc. In some embodiments, for example, the first layer 220 may be a thin, low-stiffness layer with a low Young's modulus, (e.g., less than 100 MPa).

As shown in FIGS. 2A and 2B, the second layer 224 can be configured as an acoustic window disposed on or near the first layer 220. As those of ordinary skill in the art will appreciate, the second layer 224 can be a low acoustic loss, durable layer and can robustly protect the transducer 201 from impacts and/or exposure to contaminants while also protecting a subject (e.g., a human patient, a small animal, etc.) from a excessive heat and/or charge produced by the transducer 201. The second layer 224 may be made from any lens material known in the art suitable for use with ultrasonic imaging such as, for example, a plastic, a plastic composite, a polymer, etc. In some embodiments, for example, the second layer 224 may be made from a thermoset crosslinked styrene copolymer (e.g., Rexolite) and/or polymethylpentene (e.g., TPX).

While the illustrated embodiment of FIGS. 2A and 2B is shown with only the first layer 220 and the second layer 224, more than two layers may be alternatively utilized in accordance with the disclosed technology. In some embodiments, for example, at least a third layer (not shown) with an acoustic impedance approximately between a first acoustic impedance of the first layer and a second acoustic impedance of the second layer. In other embodiments, for example, a thin composite of layers (not shown) can be used or incorporated into the transducer 200 between the first layer 220 and second layer 224. The layers within the composite of layers can include acoustic impedances that gradually change (e.g., increasing or decreasing) from the first acoustic impedance to the second acoustic impedance to improve the acoustic impedance matching between the first layer 220 and the second layer 224.

In some embodiments, the first layer 220 may have a thickness less than ¼ wavelength of a ultrasound frequency range of interest. In other embodiments, however, the first layer 220 can have a thickness any suitable fraction (e.g., 1/1, ½, ¼, ⅛, etc.) of the wavelength of ultrasound frequency of interest. In some embodiments, for example, the thickness of the first layer 220 may be chosen to be suitably thin to reduce attenuation through the first layer 220 while having a suitable thickness to allow the movement of the membrane of the transducer 201 and without being inhibited by the second layer 224. Moreover, in the illustrated embodiment, the second layer 224 is shown having a second thickness T2 greater than a first thickness T1 of the first layer 220. In other embodiments, however, the first thickness T1 may have a thickness equal to and/or greater than the second thickness T2. In some further embodiments, the first layer 220 can have varying thickness based upon, for example, performance characteristics (e.g., MUT membrane thickness, cell structural characteristics, etc) and/or frequency of ultrasound to be emitted from the transducer 201. In some embodiments, for example, the second layer 224 can be configured to be removably attached to the first layer 220 such that a plurality of different layers 224 (not shown) can be attached to the transducer 201 and the first layer 220.

As those of ordinary skill in the art will appreciate, directly bonding the second layer 224 to the transducer 201 may prevent or reduce the emission of ultrasound energy from the transducer 201. For example, disposing the second layer 224 in direct or near contact with the transducer 201 could significantly impede the movement of the membrane 108 (FIG. 2A) in response to changes in the alternating current in the array. Accordingly, placing the first layer 220 (e.g., a layer made from a compliant material) between the transducer 201 and the second layer 224 can allow movement of the membrane 108 while also improving an acoustic impedance match therebetween. In some embodiments, the first layer 220 may also be configured to adhere, bond, or otherwise couple the second layer 224 to the transducer 201.

In some other embodiments, for example, the transducer stack 200 can include additional layers. For example, an interstitial layer between the first layer 220 and the transducer 201 can include a thin material or a coated substance on the transducer 201 that can protect the transducer 201 from corrosion while being sufficiently thin to not significantly affect the performance of the transducer 201. The first layer 220 can comprise, for example, water or any other suitable liquid having an acoustic impedance that is relatively similar to the acoustic impedance of the second layer 224.

As those of ordinary skill in the art will appreciate, an acoustic impedance mismatch between the first layer 220 and the second layer 224 may cause reverberation and/or ring echoes. One way to reduce the impact of acoustic impedance mismatches is to create a textured interface between the first layer 220 and the second layer 224, as shown in, for example, FIG. 3A. Another way to reduce the impact of acoustic impedance mismatches is to configure and/or select the first layer 220 to have an acoustic impedance at least generally close to the acoustic impedance of the second layer 224 or vice versa. For example, one approach is to form the first layer 220 from a composite material that has similar acoustic impedance as the material from which the second layer 224 is formed. One of ordinary skill in the art will know that adding particles of a more dense material to the chosen first layer material can increase the density of the resulting composite and therefore the acoustic impedance as well. For example, in one embodiment, sub-micron particles can be doped into the first layer 220 to increase or decrease the mass or otherwise vary the density of the first layer 220 to be as matched as closely as possible to the second layer 224. In some other embodiments, for example, the first layer 220 can be doped with a plurality of micron-sized particles and a plurality of nano-sized particles. For example, the first layer 220 can include a low stiffness compliant material, such as, for example, silicone, and a micron-sized powder can be added to the silicone. However, merely adding the micron-sized particles to the first layer 220 may cause the micron-sized powder to settle at the bottom of the first layer 220. Accordingly, a second powder with nano-sized particles can be added to the first layer 220 to fill in the spaces between the various micron-sized particles. This is described in further detail below with reference to FIGS. 4A and 4B.

Figure 3A:
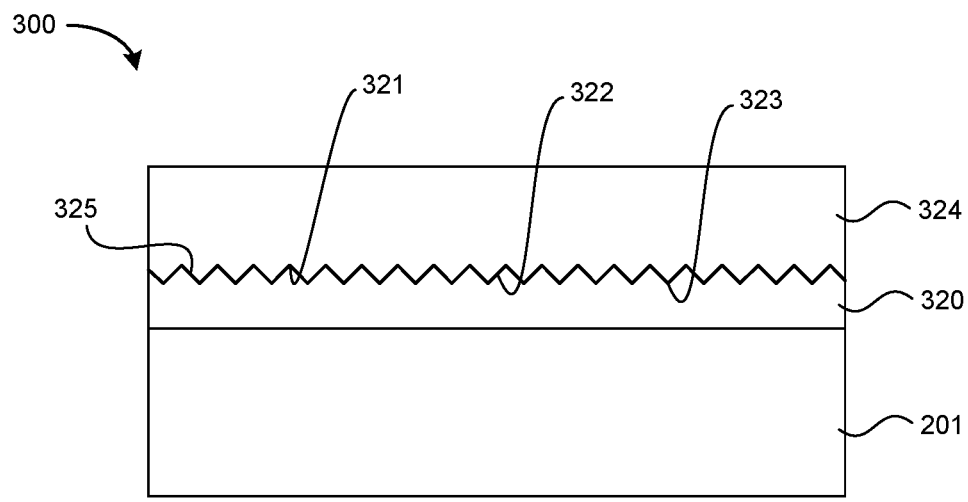
FIGS. 3A and 3B are side views of an ultrasound transducer stack configured in accordance with an embodiment of the disclosed technology.

FIG. 3A is a side view of a transducer stack 300, configured in accordance with an embodiment of the disclosure. A first layer 320 couples a second layer 324 to the transducer 201. A textured surface 325 of the second layer 324 overlies and/or contacts a top surface 321 of the first layer 320, and includes a plurality of grooves 322 and a plurality of ridges 323. The ridges 323 are configured to extend into a portion of the thickness of the first layer 320. In the illustrated embodiment, the grooves 322 and the ridges 323 extend longitudinally straight across the second layer 324. In other embodiments, however, the grooves 322 and the ridges 323 may have other patterns, such as, for example, helical, diagonal, zig-zag, etc.

As those of ordinary skill in the art will appreciate, the textured surface 325 can reduce acoustic impedance mismatches in the transducer stack 300 by providing a graduated interface between the first layer 320 and the second layer 324. The textured surface 325 may also, in some embodiments, improve adhesion between the first layer 320 and the second layer 324. As described above with reference to the first layer 220, the first layer 320 can be made from, for example, a compliant material, such as, for example, silicone or another suitable material with a low stiffness that can be bonded to the transducer 201.

Figure 3B:
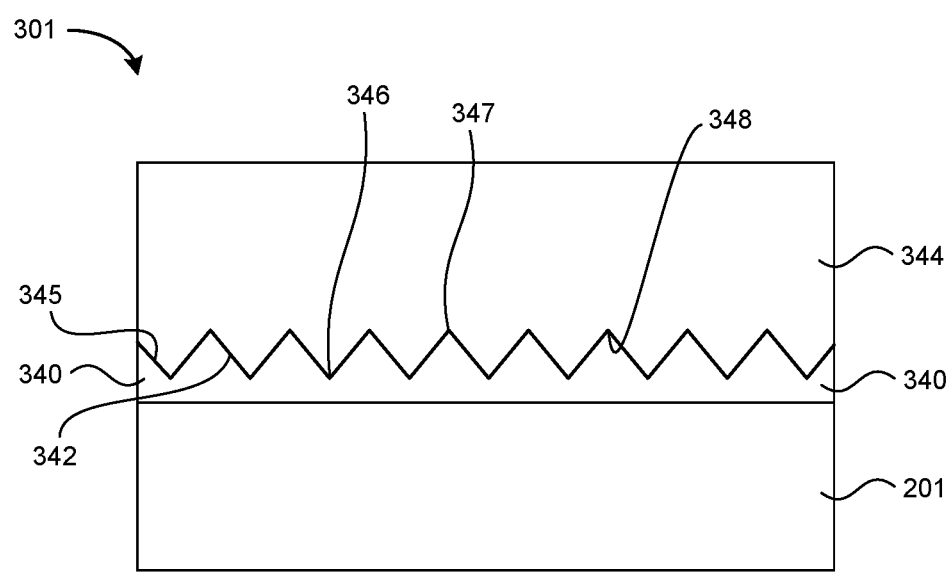

FIG. 3B is a side view of a transducer stack 301, configured in accordance with an embodiment of the disclosure. A first layer 340 couples a second layer 344 to the transducer 201. A bottom surface 345 of the second layer 344 overlies and/or contacts a top surface 342 of the first layer 340. The bottom surface 345 includes a plurality of peaks 346 and a plurality of troughs 347 with a plurality of grooves 348 formed therebetween. In the illustrated embodiment, the troughs 347 extend from the second layer 344 into the first layer 340 is approximately equal to the thickness of the first layer 340. In other embodiments, however, the troughs 347 may only extend a portion of the thickness of the first layer 340.

Figure 4A:
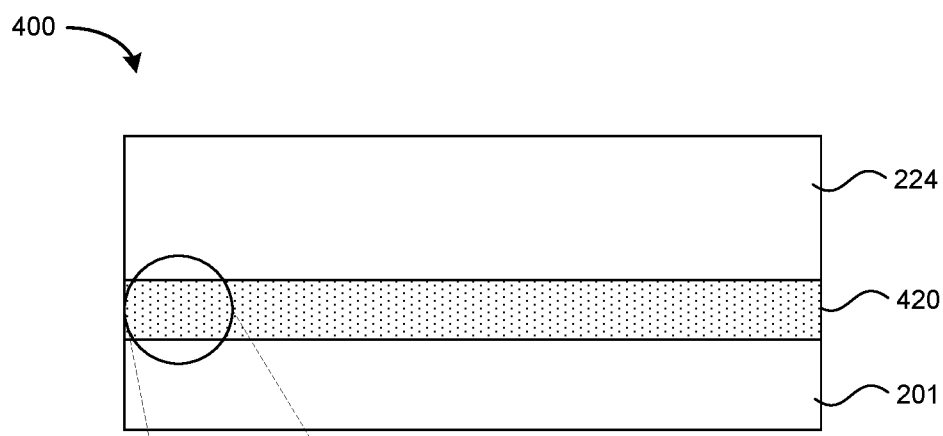
FIGS. 4A and 4B are side views of an ultrasound transducer stack configured in accordance with an embodiment of the disclosed technology.
Figure 4B:
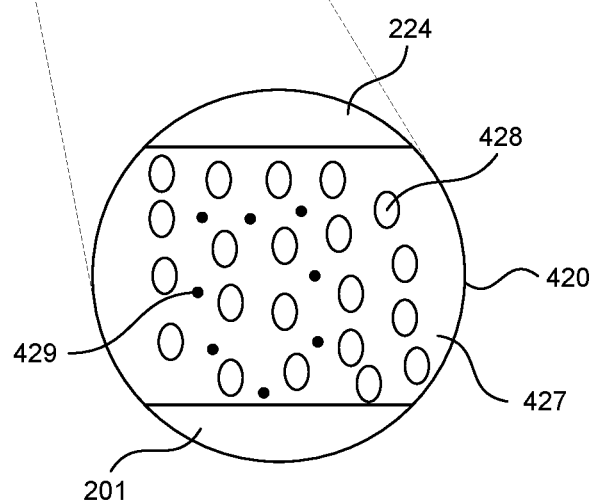

FIG. 4A is a side view of a transducer stack 400 configured in accordance with an embodiment of the present disclosure. FIG. 4B is an enlarged view of a portion of FIG. 4A. Referring to FIGS. 4A and 4B together, the transducer stack 400 includes a first layer 420 between the transducer 201 and the second layer 224. As shown in FIG. 4A, the first layer 420 can have top surface underlying a bottom surface of the second layer 224 (e.g., an acoustic lens or window). The first layer can also have a bottom surface overlying a top surface (e.g., the membrane 108 and/or the top electrode 104 of FIG. 1) of the transducer 201. The first layer 420 can be a matching layer configured for use with ultrasound having a matrix material 427 doped or filled with a first set of particles 428 (hereinafter "first particles") and a second set of particles 429 (hereinafter "second particles"). For example, in some embodiments, the matrix material 427 can be made of a compliant material (e.g., a PDMS-type silicone, an elastomer, a fluid, and/or any suitable low-stiffness material having a relatively low Young's Modulus (e.g., less than 100 MPa)), and the transducer 201 can be configured as a CMUT transducer as described with reference to FIG. 1. In other embodiments, however, the matrix material 427 may be made of an epoxy or other suitable material and the transducer 201 may be configured as a PZT transducer configured for use with ultrasound.

As explained in more detail in the U.S. Pat. No. 8,343,289, incorporated herein by reference in its entirety, the first particles 428 and/or the second particles 429 can be separately selected based on desired operating parameters (acoustic impedance, acoustic attenuation, electrical conductivity, density etc.) of the first layer 420. In some embodiments, for example, the first particles 428 may comprise micron-sized particles (e.g., greater than or equal to one micron) of a suitable first metal (e.g., tungsten, gold, platinum, alloys thereof, and/or a mixture thereof) and the second particles 429 may comprise nano-sized particles (e.g., less than one micron) of the first metal or a suitable second metal (e.g, tungsten, gold, platinum, etc.). In other embodiments, for example, the first particles 428 and the second particles 429 may be made from the same material.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein,"

"above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the disclosed technology provided herein can be applied to other systems, not necessarily the system described above. The elements and acts of the various examples described above can be combined to provide further implementations of the disclosed technology. Some alternative implementations of the disclosed technology may include not only additional elements to those implementations noted above, but also may include fewer elements.

These and other changes can be made to the disclosed technology in light of the above Detailed Description. While the above description describes certain examples of the disclosed technology, and describes the best mode contemplated, no matter how detailed the above appears in text, the disclosed technology can be practiced in many ways. Details of the system may vary considerably in its specific implementation, while still being encompassed by the disclosed technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. In general, the terms used in the following claims should not be construed to limit the disclosed technology to the specific examples disclosed in the specification, unless the above Detailed Description section explicitly defines such terms.

We claim:

1. An ultrasound transducer assembly, comprising:
    an acoustic lens comprising a lens material having a first compliance, wherein the acoustic lens is configured to be placed against a subject's skin;
    a micromachined ultrasound transducer having a second compliance; and
    an intermediate layer between the acoustic lens and the micromachined ultrasound transducer, wherein the intermediate layer comprises a first material having a compliance greater than the first and second compliances.

2. The ultrasound transducer assembly of claim 1 wherein the first material comprises an elastomeric material.

3. The ultrasound transducer assembly of claim 1 wherein the first material comprises a PDMS-type silicone.

4. The ultrasound transducer assembly of claim 1 wherein the first material has a Young's modulus less than 100 Megapascals (MPa).

5. The ultrasound transducer assembly of claim 1 wherein the first material includes a first plurality of micron-sized and a second plurality of nano-sized particles.

6. The ultrasound transducer assembly of claim 1 wherein the first material comprises a fluid.

7. The ultrasound transducer assembly of claim 1 wherein the acoustics lens is removably attached to the intermediate layer.

8. The ultrasound transducer assembly of claim 1 wherein the acoustics lens further includes a lower surface having a plurality of ridges, and wherein adjacent ridges are separated by a groove.

9. The ultrasound transducer assembly of claim 1 wherein the micromachined ultrasound transducer is a capacitive micromachined ultrasound transducer (CMUT).

10. The ultrasound transducer assembly of claim 1 wherein the micromachined ultrasound transducer is a piezoelectric micromachined ultrasound transducer (PMUT).

11. The ultrasound transducer assembly of claim 1 wherein the micromachined ultrasound transducer includes an upper portion comprising an anti-corrosive material.

12. The ultrasound transducer assembly of claim 1 wherein the first material comprises a gel.

13. The ultrasound transducer assembly of claim 1 wherein the lens material has an acoustical impedance different from an acoustical impedance of the first material.

14. A method of fabricating a micromachined ultrasound transducer assembly, the method comprising:
    attaching a first portion of an intermediate layer to a first surface of an acoustic lens, wherein the acoustic lens has a second surface opposite the first surface, and wherein the second surface is configured to be placed against a subject's skin; and
    attaching a second portion of the intermediate layer, opposite the first portion, to a micromachined ultrasound transducer, wherein the micromachined ultrasound transducer and the acoustic lens have corresponding first and second compliances, and wherein a compliance of the intermediate layer is greater than the first and second compliances.

15. The method of claim 14 wherein the intermediate layer comprises an elastomeric material.

16. The method of claim 14 wherein the intermediate layer comprises a PDMS-type silicone.

* * * * *